US009449788B2

(12) United States Patent
Fan et al.

(10) Patent No.: US 9,449,788 B2
(45) Date of Patent: Sep. 20, 2016

(54) ENHANCED DEFECT DETECTION IN ELECTRON BEAM INSPECTION AND REVIEW

(71) Applicant: KLA-Tencor Corporation, Milpitas, CA (US)

(72) Inventors: Gary G. Fan, Fremont, CA (US); Kumar Raja Guvindan Raju, Tracy, CA (US); Wade Lenn Jensen, San Jose, CA (US); Hong Xiao, Pleasanton, CA (US); Lorraine Ellen Young, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/300,631

(22) Filed: Jun. 10, 2014

(65) Prior Publication Data
US 2015/0090877 A1    Apr. 2, 2015

Related U.S. Application Data (60) Provisional application No. 61/883,995, filed on Sep. 28, 2013.

(51) Int. Cl.
*H01J 37/26*    (2006.01)
*G01N 23/225*    (2006.01)
(Continued)

(52) U.S. Cl.
CPC ......... *H01J 37/261* (2013.01); *G01N 23/2251* (2013.01); *H01J 37/265* (2013.01);
(Continued)

(58) Field of Classification Search
CPC ....................................... H01J 37/26
See application file for complete search history.

(56) References Cited

U.S. PATENT DOCUMENTS

| 5,504,017 A | 4/1996 | Yue et al. |
| 5,578,821 A | 11/1996 | Meisberger et al. |

(Continued)

FOREIGN PATENT DOCUMENTS

| EP | 0 799 903 | 10/1997 |
| EP | 2 312 302 | 4/2011 |

(Continued)

OTHER PUBLICATIONS

International Search Report and Written Opinion of the International Searching Authority for Application No. PCT/US2014/057758, Dec. 30, 2014, 7 sheets.

(Continued)

*Primary Examiner* — Jack Berman
*Assistant Examiner* — James Choi
(74) *Attorney, Agent, or Firm* — Okamoto & Benedicto LLP (57) ABSTRACT

One embodiment relates to an electron beam apparatus for inspection and/or review. An electron source generates a primary electron beam, and an electron-optics system shapes and focuses said primary electron beam onto a sample held by a stage. A detection system detects signal-carrying electrons including secondary electrons and back-scattered electrons from said sample, and an image processing system processes data from said detection system. A host computer system that controls and coordinates operations of the electron-optics system, the detection system, and the image processing system. A graphical user interface shows a parameter space and provides for user selection and activation of operating parameters of the apparatus. Another embodiment relates to a method for detecting and/or reviewing defects using an electron beam apparatus. Other embodiments, aspects and features are also disclosed.

18 Claims, 5 Drawing Sheets

(51) Int. Cl.
*H01J 37/28* (2006.01)
*H01J 37/22* (2006.01)

(52) U.S. Cl.
CPC ...... *H01J 37/28* (2013.01); *G01N 2223/6116* (2013.01); *H01J 37/222* (2013.01); *H01J 2237/004* (2013.01); *H01J 2237/24592* (2013.01); *H01J 2237/30405* (2013.01)

(56) References Cited

U.S. PATENT DOCUMENTS

| | | | |
|---|---|---|---|
| 6,217,721 B1 | 4/2001 | Xu et al. | |
| 6,777,676 B1 | 8/2004 | Wang et al. | |
| 6,801,596 B2 | 10/2004 | Nasser-Ghodsi et al. | |
| 6,924,484 B1 | 8/2005 | Wang et al. | |
| 6,996,492 B1 | 2/2006 | Testoni | |
| 7,015,467 B2 | 3/2006 | Maldonado et al. | |
| 7,030,375 B1 | 4/2006 | Testoni et al. | |
| 7,132,652 B1 | 11/2006 | Testoni | |
| 7,202,475 B1 | 4/2007 | Testoni | |
| 7,276,694 B1 | 10/2007 | Bertsche | |
| 7,425,701 B2 | 9/2008 | Steigerwald et al. | |
| 7,446,474 B2 | 11/2008 | Maldonado et al. | |
| 7,507,962 B2 | 3/2009 | Steigerwald et al. | |
| 7,643,611 B2 | 1/2010 | Shedlock et al. | |
| 7,855,159 B1 | 12/2010 | Yeckley | |
| 7,910,887 B2 | 3/2011 | Steigerwald et al. | |
| 8,045,145 B1 | 10/2011 | Bakker et al. | |
| 8,368,018 B2 | 2/2013 | Hatakeyama et al. | |
| 8,716,662 B1 * | 5/2014 | MacDonald | H01L 37/222 250/307 |
| 8,723,115 B2 | 5/2014 | Xiao et al. | |
| 2001/0016938 A1 | 8/2001 | Nishiyama et al. | |
| 2002/0036272 A1 | 3/2002 | Okino | |
| 2002/0036273 A1 | 3/2002 | Okino | |
| 2003/0094572 A1 * | 5/2003 | Matsui et al. | 250/310 |
| 2003/0155509 A1 | 8/2003 | Nakasuji et al. | |
| 2003/0204826 A1 | 10/2003 | Nishiyama et al. | |
| 2003/0206292 A1 | 11/2003 | Some | |
| 2004/0140432 A1 | 7/2004 | Maldonado et al. | |
| 2005/0087686 A1 | 4/2005 | Honda et al. | |
| 2006/0055321 A1 | 3/2006 | Maldonado et al. | |
| 2006/0097184 A1 * | 5/2006 | Frosien | 250/396 R |
| 2006/0267012 A1 | 11/2006 | Maegawa et al. | |
| 2007/0230768 A1 | 10/2007 | Adler et al. | |
| 2008/0099675 A1 | 5/2008 | Hiroi et al. | |
| 2008/0246030 A1 | 10/2008 | Satya et al. | |
| 2009/0090863 A1 | 4/2009 | Watanabe et al. | |
| 2009/0314937 A1 | 12/2009 | Sellmair | |
| 2010/0019147 A1 | 1/2010 | Hatakeyama et al. | |
| 2010/0019148 A1 | 1/2010 | Nara et al. | |
| 2010/0093022 A1 | 4/2010 | Hayworth et al. | |
| 2010/0243888 A1 | 9/2010 | Nishiyama et al. | |
| 2011/0013825 A1 | 1/2011 | Shibuya et al. | |
| 2011/0036981 A1 | 2/2011 | Zhao et al. | |
| 2011/0133066 A1 | 6/2011 | Nozoe et al. | |
| 2011/0155905 A1 | 6/2011 | Hatakeyama et al. | |
| 2012/0233542 A1 | 9/2012 | Funakoshi | |
| 2012/0287257 A1 | 11/2012 | Chino et al. | |
| 2012/0292502 A1 | 11/2012 | Langer et al. | |
| 2013/0277554 A1 * | 10/2013 | Ren | H01L 37/261 250/310 |
| 2013/0306866 A1 * | 11/2013 | Hoque et al. | 250/310 |

FOREIGN PATENT DOCUMENTS

| | | |
|---|---|---|
| JP | 11-160247 | 6/1999 |
| JP | 2006-286685 | 10/2006 |
| JP | 2010-255059 | 11/2010 |
| KR | 10-2008-0030315 | 4/2008 |
| WO | 2008066846 A2 | 6/2008 |
| WO | 2008100654 A2 | 8/2008 |
| WO | 2008134757 A1 | 11/2008 |

OTHER PUBLICATIONS

Hong Xiao, et al "Capturing Buried Defects in Metal Interconnections with Electron Beam Inspection System", 2013, 12 sheets, Proc. of SPIE vol. 8681 86810F-1, Downloaded from: http://proceedings.spiedigitallibrary.org/ on Feb. 26, 2014.

* cited by examiner

ENHANCED DEFECT DETECTION IN ELECTRON BEAM INSPECTION AND REVIEW

CROSS-REFERENCE TO RELATED APPLICATION(S)

The present application claims the benefit of U.S. Provisional Patent Application No. 61/883,995, filed Sep. 28, 2013, the disclosure of which is hereby incorporated by reference.

BACKGROUND OF THE INVENTION

1. Field of the Invention

The present invention relates to methods and apparatus for inspection and/or review of semiconductor wafers and other manufactured substrates.

2. Description of the Background Art

Semiconductor manufacturing involves various processes. Common processes include those that form microscopic features on the substrate being manufactured. The microscopic features may comprise dielectric or metallic materials, for example.

SUMMARY

One embodiment relates to an electron beam apparatus for inspection and/or review. An electron source generates a primary electron beam, and an electron-optics system shapes and focuses said primary electron beam onto a sample held by a stage. A detection system detects signal-carrying electrons including secondary electrons and back-scattered electrons from said sample, and an image processing system processes data from said detection system. A host computer system that controls and coordinates operations of the electron-optics system, the detection system, and the image processing system. A graphical user interface shows a parameter space and provides for user selection and activation of operating parameters of the apparatus.

Another embodiment relates to a method for detecting and/or reviewing defects using an electron beam apparatus. A primary electron beam is generated using an electron source, and said primary electron beam is shaped and focused onto a sample using an electron-optics system. Signal-carrying electrons, including secondary electrons and back-scattered electrons, are detected from said sample using a detection system, and data from said detection system is processed using an image processing system. Operations of the electron-optics system, the detection system, and the image processing system are controlled using a host computer system. A graphical user interface shows a parameter space and provides for user selection and activation of operating parameters of the apparatus.

Other embodiments, aspects and features are also disclosed.

DETAILED DESCRIPTION

The present disclosure provides methods and apparatus for enhanced defect detection in electron beam inspection and review. The methods and apparatus disclosed herein may be used in, but are not limited to use in, the following modes of inspection or review: 1) a swathing mode, where an electron beam scans on a sample while the sample is moving, where the direction of the scanning is nominally perpendicular to that of the sample motion; and 2) step-and-scan mode, where an electron beam scans on a sample which is nominally stationary while the beam is scanning.

The present disclosure provides methods and apparatus for enhanced detection of defects, including the following types: 1) material contrast defects; 2) buried defects, including buried voids and buried material contrast defects; 3) in-trench defects, which may be at the bottom of a deep, high-aspect-ratio trench or contact hole; 4) voltage contrast defects; and 5) nanometer-scale physical defects.

Figure 1:
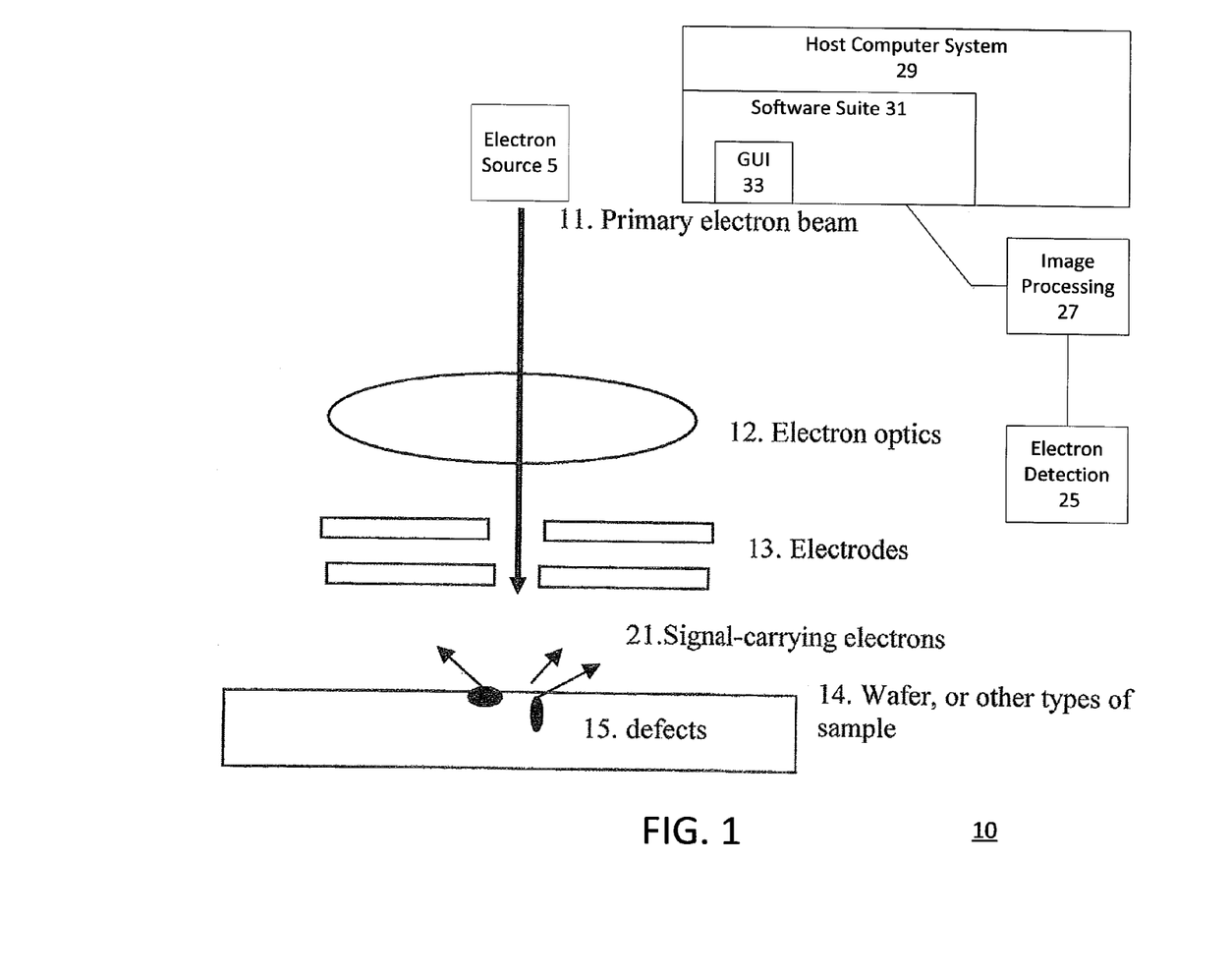
FIG. 1 is a schematic diagram of an electron beam apparatus for defect detection and review in accordance with an embodiment of the invention.

FIG. 1 is a cross-sectional diagram of an electron beam apparatus 10 for defect detection and review in accordance with an embodiment of the invention. As shown, the apparatus includes a primary electron beam 11 that may be generated by an electron source 5 and may have an energy up to 15 keV (kilo-electron-volts).

The primary electron beam 11 may be focused by the electron optics 12 and may be further shaped by a plurality of electrodes 13 before landing upon the surface of a sample 14. The sample 14 may be a silicon wafer or other type of sample. The sample 14 may be have circuit-related structures manufactured, or in the process of being manufactured, thereon or therein.

The landing energy of the primary electron beam 11 may be controlled by biasing the sample to a desired voltage relative to the electron source. The landing energy may be controlled so as to vary from 0 eV (electron-volts) to 30 keV.

Interactions between the primary electron beam 11 and the sample 14, with defects 15 on or near the surface of the sample 14, as well as within the sample 14, result in the release of secondary electrons, back-scattered electrons, an other forms of signal-carrying electrons 21. These signal-carrying electrons 21 may be detected by one or more electron detectors 25.

The apparatus 10 further includes: a detection system 25 that detects signal-carrying electrons including secondary electrons and back-scattered electrons from said sample; an image processing system 27 that processes data from said detection system; a host computer system 29 that controls and coordinates operations of aforementioned systems and their subsystems; and a suite of computer software 31 including a graphical user interface 33 which shows the parameter space, and enables users to select and activate the operating parameters of said electron beam inspection and review apparatus.

Figure 2:
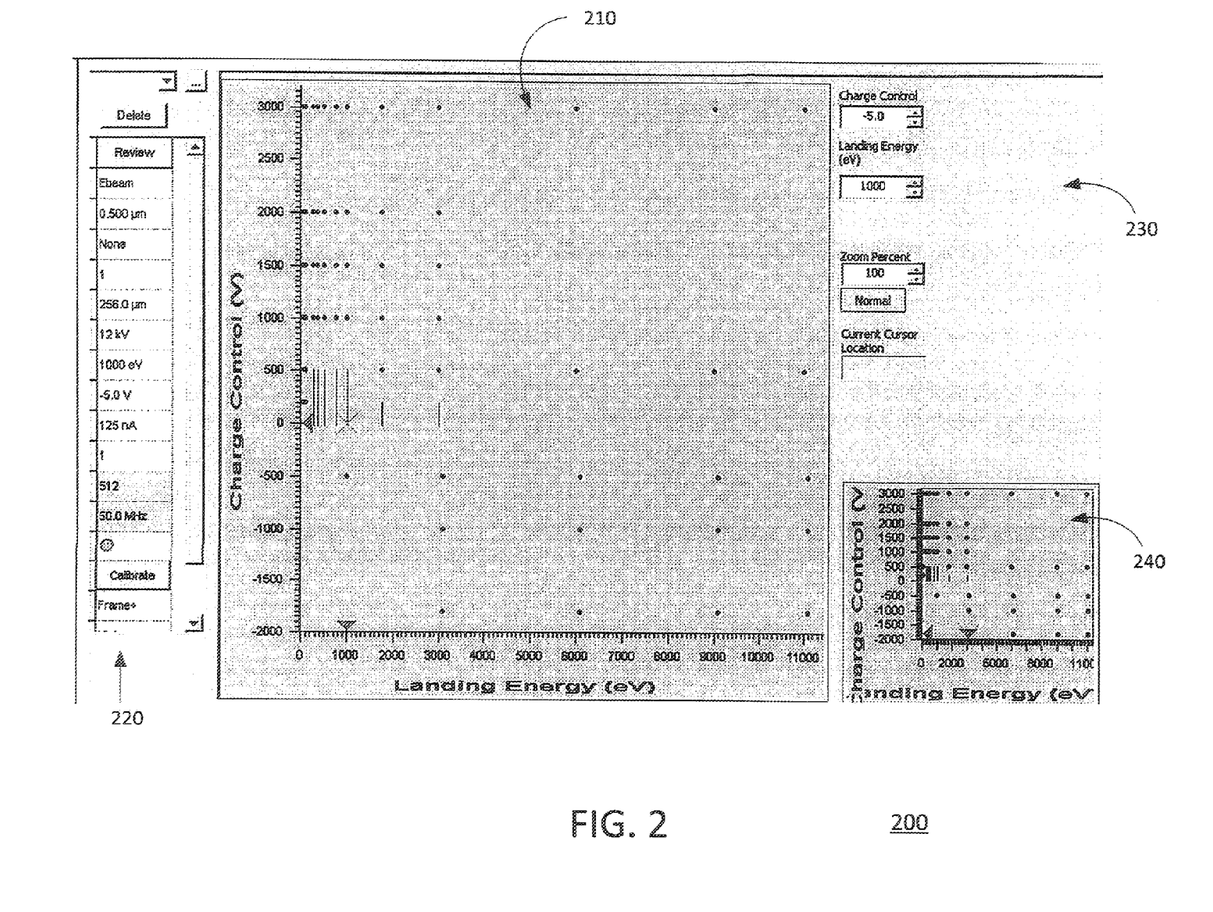
FIG. 2 depicts a graphical user interface for selecting an operating point in parameter space in accordance with an embodiment of the invention.

FIG. 2 depicts a graphical user interface 200 for selecting an operating point in parameter space in accordance with an embodiment of the invention. As described below, this graphical user interface 200 provides an advantageous technique of selecting the operating point from allowed discrete points and allowed ranges in the parameter space.

The Cartesian coordinate system in the main graph 210 shows a zoom view of the parameter space of said apparatus 10: the horizontal axis is the landing energy (in eV); and the vertical axis is the charge control voltage (in volts or V). The charge control voltage indicates the nominal voltage difference between the wafer 14 and the electrode 13 which is closest to the wafer. The current (active) operating point (charge control at −5.0 volts and landing energy at 1000 eV) is indicated in the graph 210 by an "X" cross mark and by the corresponding arrowheads (triangles) pointing to the corresponding positions on the vertical and horizontal axes. The current operating point is the same in FIGS. 2, 3 and 4.

The other operating parameters, including the beam current in the incident beam, are shown in the display column 220 to the left of the graph 210. Going from top to bottom, the operating parameters shown, below "Review," include: Image Type ("Ebeam"); Pixel Size ("0.500 µm"); Adaptive Pixel Mode ("None"); Adaptive Pixel Scale ("1"); Field of View ("256.0 µm"); Beam Energy ("12 kV"); Landing Energy ("1000 eV"); Charge Control ("−5.0 V"); Beam Current ("125 nA"); Scan Averages ("1"); Scan Height ("512"); Scan Rate ("50.0 MHz"); and, under "Calibrate," Averaging Mode ("Frame+").

On the upper right of the interface 200, there is provided selection controls 230 for Charge Control (V) ("−5.0"), Landing Energy (eV) ("1000"), and Zoom Percent (%) ("100"). On the lower right of the interface 200, there is provided a zoom-control overview 240 of the operating parameter space. In the example shown in FIG. 2, the zoom percent is 100% so that region of parameter space shown in the zoom-control (overview) graph 240 and the zoom-view (main) graph 210 are the same, though greater detail is shown in the zoom-view graph 210.

In both the zoom-view (main) graph 210 the zoom-control (overview) graph 240, points in the graphs are discrete "legal" (i.e. allowed) operating points (i.e. a specific charge control voltage and a specific landing energy), whereas lines in the graphs indicate continuous operating ranges that are "legal" (i.e. allowed). As depicted, for example, a vertical line segment in the graph allows a range of charge control voltages at a discrete landing energy.

Figure 3:
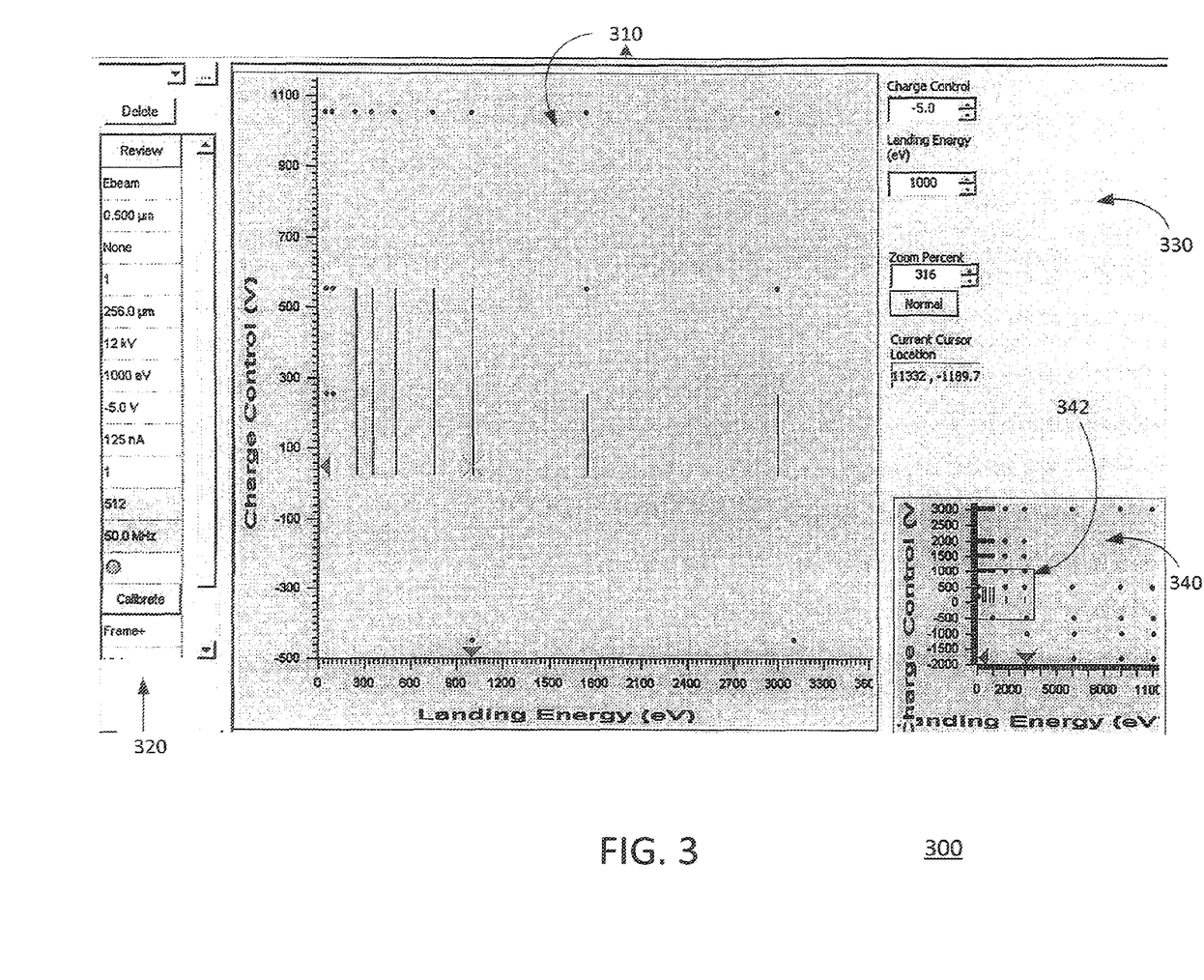
FIG. 3 depicts the graphical user interface with a zoom-in view of the parameter space in accordance with an embodiment of the invention.

FIG. 3 depicts the graphical user interface 300 with a zoom-in view of the parameter space in accordance with an embodiment of the invention. In FIG. 3, the operating parameters in the display column 310 on the left are the same as the operating parameters in the display column 220 on the left in FIG. 2.

The zoom-view graph 310 in FIG. 3 is at zoom of 316%, as indicated in the selection controls 330. The current (active) operating point is indicated by the "X" cross mark and by the corresponding arrowheads (triangles) pointing to the corresponding positions on the vertical and horizontal axes. In FIG. 3, the current cursor location ("11332, −1189.7") in the Cartesian coordinate system is indicated under the selection controls 330. This current cursor location in the user interface may be moved and selected via a point-and-click device to select a new operating point.

The region of parameter space shown in the zoom-view graph 310 is indicated by the rectangle 342 shown within the zoom-control graph 340. The position and size of the rectangle 342 within the zoom-control graph 340 is controllable by way of the interface.

Like in FIG. 2, points in the zoom-view and zoom-control graphs (310 and 340) in FIG. 3 are discrete "legal" (i.e. allowed) operating points (i.e. a specific charge control voltage and a specific landing energy), whereas lines in the zoom-view and zoom-control graphs (310 and 340) indicate continuous operating ranges that are "legal" (i.e. allowed). As depicted, for example, a vertical line segment in the graph allows a range of charge control voltages at a discrete landing energy.

Figure 4:
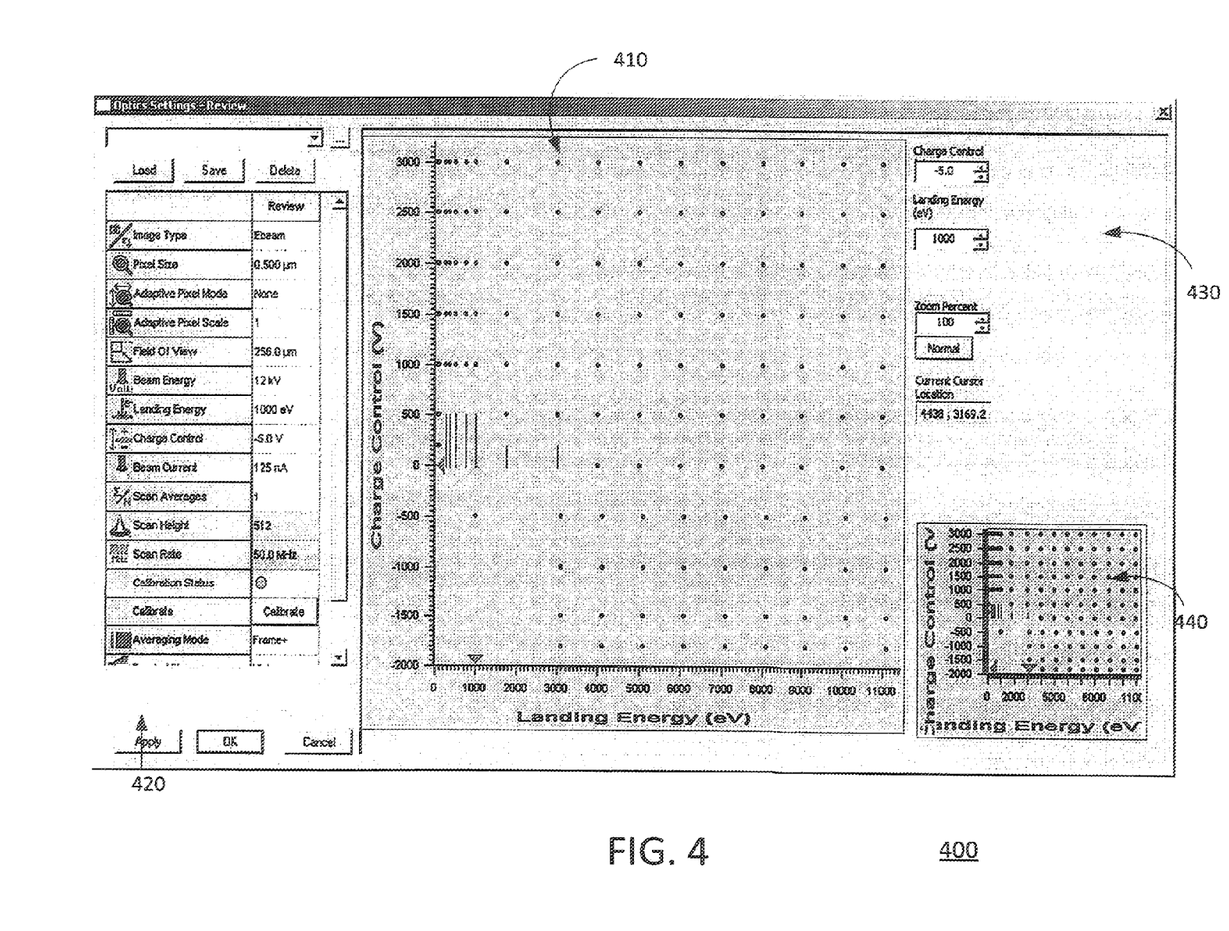
FIG. 4 depicts a graphical user interface for selecting an operating point in parameter space with regions of the parameter space containing regular grid points in accordance with an embodiment of the invention.

FIG. 4 depicts a graphical user interface 400 for selecting an operating point in parameter space with regions of the parameter space containing regular grid points in accordance with an embodiment of the invention. The interface 400 shown in FIG. 4 is similar to the interface 200 shown in FIG. 2. The interface 400 shown in FIG. 4 includes a zoom-view graph 410, an operating-parameter display column 420, selection controls 430, and a zoom-control graph 440.

In addition, the zoom-view and zoom-control graphs (410 and 440) of FIG. 4 include further operating points on a regular grid (i.e. on a grid with periodic spacing in the horizontal and vertical dimensions). These regular grid points are in addition to the operating points and lines depicted in the zoom-view and zoom-control graphs (210 and 240) of FIG. 2. Furthermore, the interface 400 of FIG. 4 shows the labels for the operating parameters in the display column 420 to the left of the zoom-view graph 410.

Figure 5:
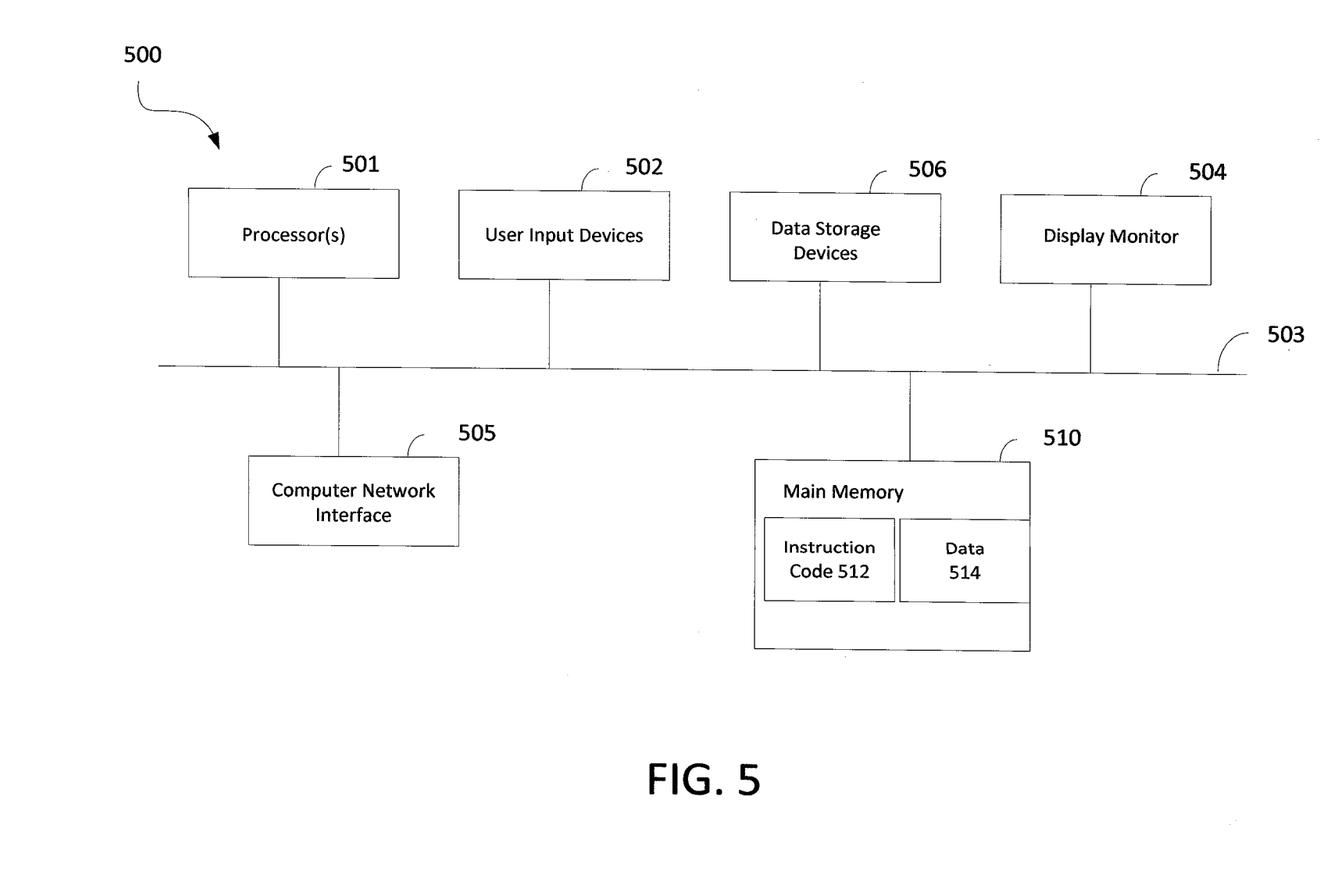
FIG. 5 depicts a simplified form of an example computer, including computer software, for controlling the electron beam apparatus in accordance with an embodiment of the invention.

FIG. 5 depicts a simplified form of an example computer 500, including computer software, for controlling the electron beam apparatus in accordance with an embodiment of the invention. Such a computer may be used, for example, to implement and perform the methods described above. This figure shows just one simplified example of such a computer.

As shown, the computer 500 may include one or more processors 501, such as those from the Intel Corporation of Santa Clara, Calif., for example. The computer 500 may have one or more buses 503 communicatively interconnecting its various components. The computer 500 may include one or more user input devices 502 (e.g., keyboard, mouse, etc.), a display monitor 504 (e.g., liquid crystal display, flat panel monitor, etc.), a computer network interface 505 (e.g., network adapter, modem), and a data storage system that may include one or more data storage devices 506 which may store data on a hard drive, semiconductor-based memory, optical disk, or other tangible non-transitory computer-readable storage media, and a main memory 510 which may be implemented using random access memory, for example.

In the example shown in this figure, the main memory 510 includes instruction code 512 and data 514. The instruction code 512 may comprise executable computer-readable program code (i.e., software) components which may be loaded from the tangible non-transitory computer-readable medium of the data storage device 506 to the main memory 510 for execution by the processor(s) 501. In particular, the instruction code 512 may be programmed to cause the computer 500 to control the electron beam apparatus 10 and provide the graphical user interfaces as described herein.

Inventive aspects disclosed herein include the following:

Inventive Aspect 1: An electron beam inspection and review apparatus including: an electron source that generates a primary electron beam; a stage which carries a sample to be inspected or reviewed; an electron optics system that shapes and focuses said primary electron beam onto said sample; a detection system that collectively or selectively detects signal-carrying electrons including secondary electrons and back-scattered electrons from said sample; an image processing system that processes data from said detection system; a host computer system that controls and coordinates operations of aforementioned systems and their subsystems; and a suite of computer software including a graphical user interface which shows the parameter space, and enables users to select and activate the operating parameters of said electron beam inspection and review apparatus.

Inventive Aspect 2. The electron beam inspection and review apparatus according to Inventive Aspect 1, wherein said electron optics system comprises a plurality of electron lenses, a plurality of electrodes above said sample; voltages are applied to said electrodes and said sample in such a way that a charge control voltage is created between the sample and the electrode which is closest to the sample; said charge control voltage is treated as an independent operating parameter to extract or reject, collectively or selectively, aforementioned signal-carrying electrons; said charge control voltage has a range of at least from −1 kV to +1 kV. In one implementation, for example, said charge control voltage has a range from −15 kV to +15 kV.

Inventive Aspect 3. The electron beam inspection and review apparatus according to Inventive Aspect 2, wherein said landing energy is also treated as an independent operating parameter and has a range of at least from 0 eV to 11 keV. In one implementation, for example, said landing energy has a range from 0 eV to 30 keV. In this implementation, said primary electron beam has an energy range from 0 eV to 15 keV, and said sample is biased from −15 kV to +15 kV, resulting in a net landing energy ranging from 0 eV to 30 eV when said primary electron beam lands on said sample.

Inventive Aspect 4. The electron beam inspection and review apparatus according to Inventive Aspect 3, wherein said landing energy and said charge control voltage are represented by the horizontal and vertical axis, respectively or arbitrarily, in a 2-dimensional parameter space in a user graphic interface. Said parameter space shows the current operating point, and allows users to select a new operating point by clicking in the Cartesian coordinate.

Inventive Aspect 5. The electron beam inspection and review apparatus according to Inventive Aspect 4, wherein said landing energy and charge control voltage can be varied continuously, so that any point in the Cartesian coordinate can be selected as the operating point.

Inventive Aspect 6. The electron beam inspection and review apparatus according to Inventive Aspect 4, wherein said landing energy and charge control voltage are discrete, each can be varied in increments of 100V or 100 eV, whichever unit is applicable, thus forming a 2 dimensional grid in the Cartesian coordinate.

Inventive Aspect 7. The electron beam inspection and review apparatus according to Inventive Aspect 4, wherein regions of the said parameter space is continuous, whereas others are discrete.

Inventive Aspect 8. The electron beam inspection and review apparatus according to Inventive Aspect 7, wherein yet other regions of the said parameter space is continuous along one axis only.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. An electron beam apparatus for inspection and/or review, the apparatus comprising:
   an electron source that generates a primary electron beam;
   a stage which carries a sample;
   an electron-optics system that shapes and focuses said primary electron beam onto said sample;
   a detection system that detects signal-carrying electrons including secondary electrons and back-scattered electrons from said sample;
   an image processing system that processes data from said detection system;
   a host computer system that controls and coordinates operations of the electron-optics system, the detection system, and the image processing system; and
   a graphical user interface which displays a parameter space and provides for user selection and activation of operating parameters of the apparatus,
   wherein the parameter space displayed by the graphical user interface is a two-dimensional parameter space that has a first dimension comprising a charge control voltage and a second dimension comprising a landing energy,
   wherein the two-dimensional parameter space includes both continuously-variable regions displayed as lines in the two-dimensional parameter space and discretely-variable regions displayed as points in the two-dimensional parameter space, and
   wherein said user selection and activation of said operating parameters comprises selecting an operating point from allowed points in the two-dimensional parameter space by pointing and clicking on the operating point using the graphical user interface.

2. The apparatus of claim 1, wherein said electron-optics system comprises:
   a plurality of electrodes above said sample,
   wherein voltages are applied to said electrodes and said sample in such a way that said charge control voltage is created between the sample and the electrode which is closest to the sample, and
   wherein said charge control voltage is an independent operating parameter that is controllable by way of the graphical user interface.

3. The apparatus of claim 2, wherein said charge control voltage is selected to filter the signal-carrying electrons to extract back-scattered electrons and reject secondary electrons.

4. The apparatus of claim 2, wherein said charge control voltage is selected to filter the signal-carrying electrons to reject back-scattered electrons and extract secondary electrons.

5. The apparatus of claim 2, wherein said charge control voltage is selected to filter the signal-carrying electrons to extract a mixture of back-scattered electrons and secondary electrons.

6. The apparatus of claim 2, wherein said charge control voltage ranges at least from −1 kilovolts to +1 kilovolts.

7. The apparatus of claim 2, wherein the primary electron beam lands on said sample with said landing energy, and wherein said landing energy is an independent operating parameter that is controllable by way of said graphical user interface.

8. The apparatus of claim 7, wherein said landing energy ranges at least from 0 electron-volts to 11 kilo-electron-volts.

9. The apparatus of claim 1, wherein said parameter space shows a current operating point and provides for selection of a new operating point by pointing and clicking on the new operating point in said parameter space.

10. The apparatus of claim 9, wherein said landing energy and said charge control voltage are continuously variable so that any point in said parameter space is selectable as the new operating point.

11. The apparatus of claim 9, wherein said landing energy and said charge control voltage are discretely variable in fixed increments within said parameter space.

12. The apparatus of claim 11, wherein the fixed increments include a 100 volt increment for said charge control voltage and a 100 electron-volt increment for said landing energy.

13. The apparatus of claim 1, wherein a continuously-variable region comprises a continuous range in the first dimension in said parameter space at discrete values along the second dimension in said parameter space.

14. The apparatus of claim 13, wherein the first dimension is said charge control voltage, and the second dimension is said landing energy.

15. A method of detecting and/or reviewing defects using an electron beam apparatus, the method comprising:
generating a primary electron beam using an electron source;
carrying a sample using a stage;
shaping and focusing said primary electron beam onto said sample using an electron-optics system;
detecting signal-carrying electrons including secondary electrons and back-scattered electrons from said sample using a detection system;
processing data from said detection system using an image processing system;
controlling operations of the electron-optics system, the detection system, and the image processing system using a host computer system; and
displaying a parameter space and providing for user selection and activation of operating parameters of the apparatus using a graphical user interface,
wherein the parameter space displayed by the graphical user interface is a two-dimensional parameter space that has a first dimension comprising a charge control voltage and a second dimension comprising a landing energy,
wherein the two-dimensional parameter space includes both continuously-variable regions displayed as lines in the two-dimensional parameter space and discretely-variable regions displayed as points in the two-dimensional parameter space, and
wherein said user selection and activation of said operating parameters comprises selecting an operating point from allowed points in the two-dimensional parameter space by pointing and clicking on the operating point using the graphical user interface.

16. The method of claim 15, wherein said electron-optics system comprises a plurality of electron lenses and a plurality of electrodes above said sample, further comprising:
applying voltages to said electrodes and said sample in such a way that said charge control voltage is created between the sample and the electrode which is closest to the sample; and
controlling said charge control voltage as a first independent operating parameter by way of said graphical user interface.

17. The method of claim 16, wherein the primary electron beam lands on said sample with said landing energy, further comprising:
controlling said landing energy as a second independent operating parameter by way of said graphical user interface.

18. The method of claim 17, further comprising:
indicating a current operating point by a mark in said parameter space; and
providing for selection of a new operating point by pointing and clicking on the new operating point in said parameter space.

* * * * *